United States Patent [19]
Oku et al.

[11] Patent Number: 5,287,733
[45] Date of Patent: Feb. 22, 1994

[54] APPARATUS FOR RECEIVING LIQUID TREATMENT SAMPLES FOR DISPOSAL

[75] Inventors: Narihiro Oku; Hitoshi Mitani; Hiroaki Takahasi, all of Kyoto, Japan

[73] Assignees: Horiba Ltd., Kyoto, Japan; ABX S.A., Montpellier, France

[21] Appl. No.: 765,151

[22] Filed: Sep. 23, 1991

[30] Foreign Application Priority Data

Sep. 23, 1990 [JP] Japan .................................. 2-253049

[51] Int. Cl.$^5$ .................... G01N 33/48; G01N 35/00
[52] U.S. Cl. .................................. 73/64.56; 422/81
[58] Field of Search ............... 73/61.41, 64.56, 863.02, 73/863.01; 141/94, 95; 422/73, 67, 81; 436/43, 50, 66

[56] References Cited

U.S. PATENT DOCUMENTS

| | | | |
|---|---|---|---|
| 3,812,890 | 5/1974 | Haas et al. | 141/94 |
| 4,030,888 | 6/1977 | Yamamoto et al. | 422/73 |
| 4,121,907 | 10/1978 | Roque | 422/81 |
| 4,273,742 | 6/1981 | Huber et al. | 422/81 |
| 4,740,356 | 4/1988 | Huber | 436/43 |
| 4,860,804 | 8/1989 | Yamaguchi et al. | 141/65 |
| 4,922,975 | 5/1990 | Polaschegg | 141/94 |
| 5,094,818 | 3/1992 | Longman et al. | 422/73 |

FOREIGN PATENT DOCUMENTS

2562881 10/1985 France .................................. 141/94

*Primary Examiner*—Hezron E. Williams
*Assistant Examiner*—Michael Brock
*Attorney, Agent, or Firm*—Price, Gess & Ubell

[57] ABSTRACT

A system collects fluid waste within a closed waste vessel where a waste disposal cycle is determined based upon the pressure level within the waste vessel. In the preferred embodiment, a closed liquid waste vessel accepts waste solutions through conduits having valves controlling conduit fluid communication with treatment vessels. A pressure sensor determines the level of pressure within the waste vessel. A pressurizing device reduces the level of pressure within the vessel. When the pressure within the vessel is lowered to a predetermined level, the valve is opened. When the pressure sensed within the liquid waste vessel then rises above an appointed value, the valve is closed, completing the waste collection of a treated sample. This corresponds to the point in time when the treatment vessel is empty, allowing a sudden rush of air into the waste vessel, raising the vessel pressure to ambient and closing the valve. When the pressure in the waste vessel does not rise to the appointed value after the lapse of a preset length of time, a warning signal is provided advising that the system is not working properly.

6 Claims, 3 Drawing Sheets

APPARATUS FOR RECEIVING LIQUID TREATMENT SAMPLES FOR DISPOSAL

FIELD OF THE INVENTION

The present invention relates to an apparatus for measuring liquid and, specifically, to an apparatus for the waste, storage, and treatment of measured blood samples.

BACKGROUND OF THE INVENTION

FIG. 3 shows a block diagram of a conventional blood corpuscle measuring and disposal system. In FIG. 3, a lower end of sample nozzle 1 may be immersed in a blood sample 2 to be measured. A predetermined quantity of blood is removed from the sample 2 by the sample nozzle 1 when a constant volume syringe 4 provides a negative pressure within the sample nozzle 1 through tube 3. The constant volume syringe 4 is a pump composed of a cylinder and a piston.

An elevating device 5 elevates the sample nozzle 1 with respect to the blood sample 2. The elevating device 5 uses a stepping motor M as a drive source. The sample nozzle 1 is raised from the sample 2 to an appointed height, as shown by arrow A in FIG. 3.

A rinsing device 6 rinses the outer circumference of the sample nozzle 1 as the sample nozzle 1 is removed from the sample 2 by elevating device 5. Thus, blood stuck to the outer circumference of sample nozzle 1 is cleaned.

A transfer device 7 horizontally transfers the sample nozzle 1 in the direction B once the sample nozzle 1 has been raised to a sufficient height above the sample 2 by elevating device 5. Once the sample nozzle 1 is horizontally moved to a position above mix cell 8, the blood within sample nozzle 1 is expelled into mix cell 8. The blood is released when the constant volume syringe 4 provides a positive pressure within sample nozzle 1 through connection tube 3.

Mix cell 8 is a vessel wherein blood is subjected to primary treatment for the measurement of blood corpuscles. In this primary treatment, a physiological solution of salt is added as a diluent to the blood, and an anticoagulant is added to the blood such as ethylene diamine tetraacetic acid (EDTA).

The primary treated blood (hereinafter referred to as the "solution") is then provided to a white blood corpuscle (WBC) cell 9 and a red blood corpuscle (RBC) cell 10 from the mix cell 8. The WBC cell 9 receives solution supplied from the mix cell 8 to subject it to further treatment for a measurement of white blood corpuscles. In the white corpuscle treatment, a blood dissolving agent is added to destroy red blood corpuscles. Additionally, cyan is added to enable the measurement of the concentration of hemoglobin in the blood sample. The Hgb concentration measurement is conducted after the measurement of the white blood corpuscle count.

A counter 11 is annexed to the WBC cell 9 for counting the number of white blood corpuscles in the solution which has been subjected to the WBC treatment. For example, an electric resistance change detecting device may be used to determine the white blood corpuscle count or concentration.

The red blood corpuscle cell 10 also receives solution from the mix cell 8. However, the red blood corpuscle cell 10 subjects the solution to a treatment including the measurement of red blood corpuscles.

Since the number of red blood corpuscles in blood is generally about 500 times that of white blood corpuscles, a secondary dilution treatment is necessary. In the secondary dilution treatment, the solution is further diluted approximately 100 times so that an error which may be due to white blood corpuscles is then within a range of an error of measurement.

A blood corpuscle counter 12 is annexed to the RBC cell 10 in order to count the number of red blood corpuscles treated in the RBC cell 10. The red blood corpuscle counter 12 uses the same electric resistance change detecting method used by white blood corpuscle counter 11. Furthermore, the mean size of the red blood corpuscles and the number of blood platelets having a volume smaller than the red blood corpuscles are measured.

An Hgb-measuring device 13 is used to measure the concentration of hemoglobin in the blood treated in WBC cell 9. The hemoglobin measuring device 13 includes a light-transmissive flow cell, which accepts and stores a quantity of solution from WBC cell 9 to hold the solution between a light source and a photodiode. Cyan is added to the solution in WBC cell 9 and combined with the hemoglobin, resulting in cyan methohemoglobin. Cyan methohemoglobin exhibits a high absorptivity for light at a wavelength of approximately 540 nanometers such that the light transmission intensity will be reduced in accordance with an increase of the concentration of the hemoglobin.

Once the various measuring operations are conducted in WBC cell 9, hemoglobin measuring device 13 and RBC cell 10, the various used waste solutions are fed into waste cell 14 for disposal. The waste cell 14 is a closed vessel which communicates with WBC cell 9, Hgb measuring device 13, and RBC cell 10 through conduits 16a, 16b and 16c provided with electromagnetic valves 15a, 15b, and 15c, respectively. The waste cell 14 is also provided with vacuum pump 17 which reduces the internal pressure within the waste cell 14 to a predetermined value.

During the processing of the solutions, the electromagnetic valves 15a, 15b, 15c are opened by valve controlling device 18 so that the solution within the WBC cell 9, RBC cell 10, and Hgb measuring device 13 are sucked into the depressurized waste cell 14 through the conduits 16a, 16b, and 16c, respectively.

The valve controlling device 18 works on a time clock. Once a predetermined time period has lapsed from the beginning of the waste collection of the treated solutions, the electromagnetic valves 15a, 15b, and 15c are closed by the valve controlling device 18. Thus, the waste solution collection is completed within a preset time estimated to be sufficient for collecting all of the treated solutions into waste cell 14.

In the above-described conventional apparatus, the time dependency is unable to account for the quantity of solution being collected from the various treatment cells. If there is less solution than estimated, the valves 15a, 15b, and 15c remain open too long. If there is more solution than estimated, the valves are not open long enough. The more beneficial case in this regard is when the valves are left open too long in order to ensure the completion of the waste collection. However, this reduces the efficiency of the operation if blood measurements are to be made continuously, one after the other.

Furthermore, it is impossible to detect a clogging of the conduits 16a, 16b, and 16c.

OBJECTS OF THE INVENTION

It is therefore an object of the present invention to provide a waste collection and treatment apparatus which is capable of efficiently receiving liquid treatment samples for disposal.

It is yet a further object of the invention to provide a waste collection and treatment apparatus which allows the efficient repetitive disposal of solutions which have been treated within a solution treatment apparatus.

It is yet still a further object of the invention to provide an efficient fluid waste disposal apparatus which may be used in conjunction with the treatment of blood.

It is yet a still further object of the present invention to provide a fluid waste disposal apparatus which is capable of automatically detecting the clogging of fluid conduits.

SUMMARY OF THE INVENTION

These and other objects of the invention are provided for by a system which collects fluid waste within a closed waste vessel where the waste disposal cycle is determined based upon the pressure level within the waste vessel.

In the preferred embodiment of the invention, a closed liquid waste vessel accepts waste solutions through conduits having valves controlling conduit fluid communication with treatment vessels. A pressure sensor determines the level of pressure within the waste vessel. A pressurizing device reduces the level of pressure within the vessel. When the pressure within the vessel is lowered to a predetermined level, the valve is opened.

When the pressure sensed within the liquid waste vessel then rises above an appointed value, the valve is closed, completing the waste collection of a treated sample. This corresponds to the point in time when the treatment vessel is empty, allowing a sudden rush of air into the waste vessel, raising the vessel pressure to ambient and closing the valve. When the pressure in the waste vessel does not rise to the appointed value after the lapse of a preset length of time, a warning signal is provided advising that the system is not working properly.

BRIEF DESCRIPTION OF THE DRAWINGS

The present invention, both as to its organization and manner of operation, together with further objects and advantages, may be understood by reference to the following drawings.

DETAILED DESCRIPTION OF THE PREFERRED EMBODIMENTS

The following description is provided to enable any person skilled in the art to make and use the invention and sets forth the best modes contemplated for carrying out the invention. Various modifications, however, will remain readily apparent to those skilled in the art, since the generic principles of the present invention have been defined herein.

Figure 1:
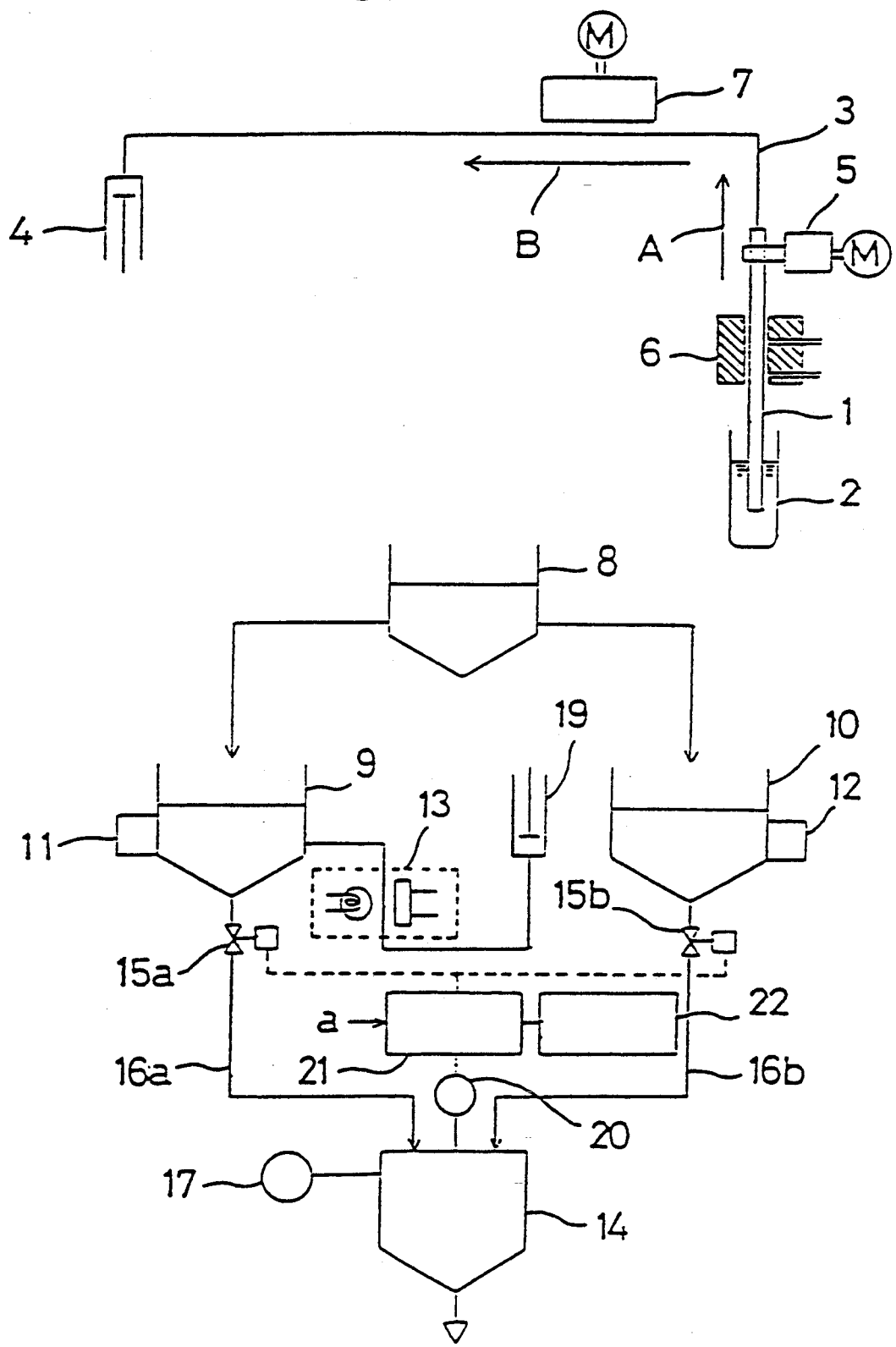
FIG. 1 is a block diagram showing a preferred embodiment of the present invention.
Figure 2:
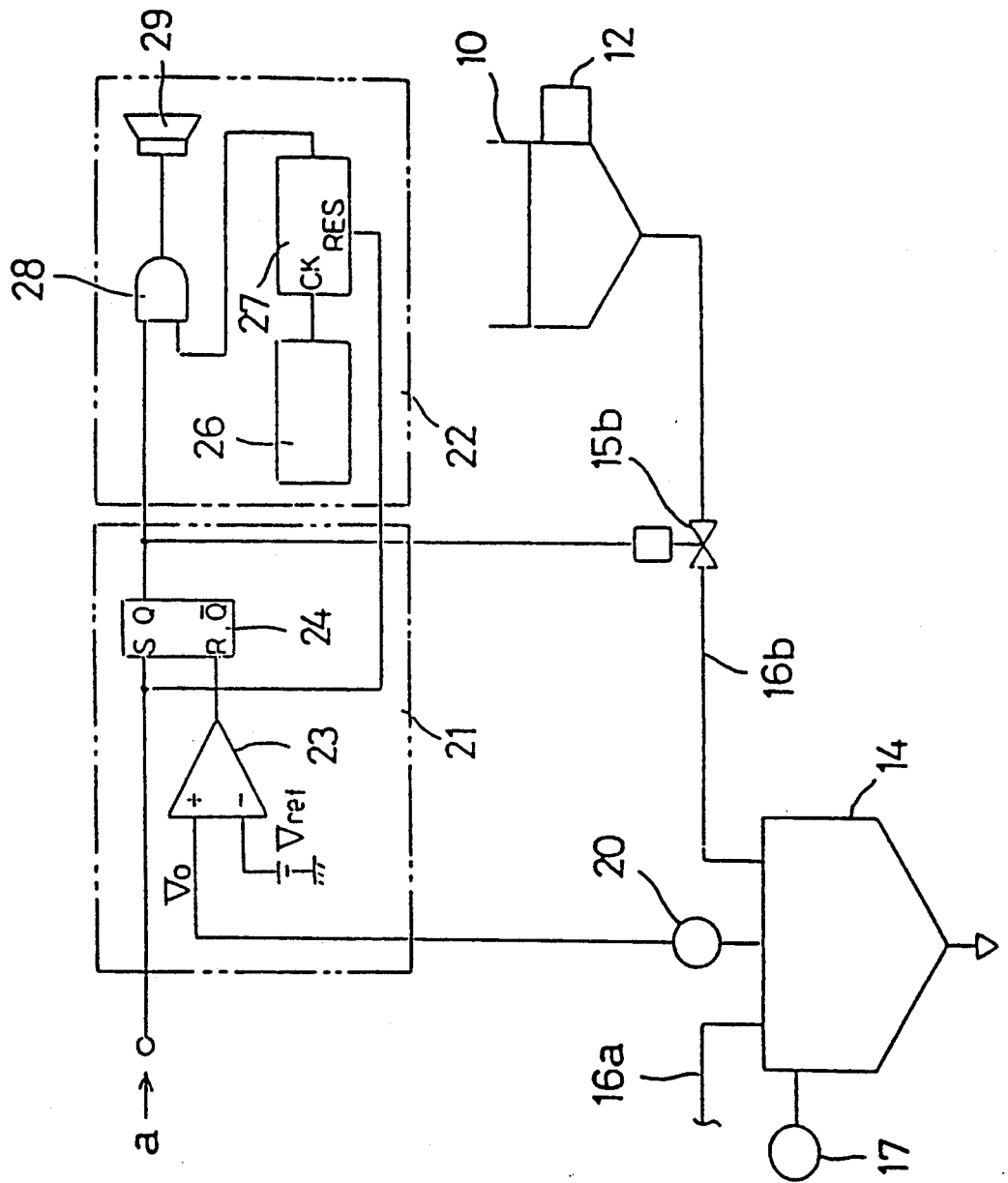
FIG. 2 is a block diagram showing a partial construction of the sample collecting mechanism in the preferred embodiment of the invention shown in FIG. 1.

FIGS. 1 and 2 are block diagrams of an apparatus which may be used for measuring blood corpuscles and disposing of the measured blood according to the present invention.

As shown in FIG. 1, a container holding a blood sample 2 is sampled by sample nozzle 1. Sample nozzle I is placed within the blood sample 2, and a negative pressure is provided within sample nozzle 1 through tube 3 by constant volume syringe 4.

Once a blood sample has been removed by sample nozzle 1, elevating device 5 elevates the sample nozzle 1 through rinsing device 6 in the direction A. Once the sample nozzle 1 has been raised to a sufficient height above the blood sample 2, conveying device 7 horizontally moves sample nozzle 1 in the direction B so that the blood sample may be expelled into mix cell 8. When sample nozzle 1 is in position above mix cell 8, a positive pressure is applied by constant volume syringe 4 expelling the blood sample into mix cell 8.

Within mix cell 8, the blood sample is subjected to a primary treatment prior to the treated blood sample being placed into the WBC cell 9 for measuring the number of white blood corpuscles, and RBC cell 10 for measuring the number of red blood corpuscles.

Blood corpuscle counters 11 and 12 are annexed to RBC cell 9 and WBC cell 10, respectively, which use an electric resistance change detecting method to count the number of blood corpuscles. An Hgb measuring device 13 measures the concentration of hemoglobin in the treated blood solution. Hgb measuring device 13 is attached to WBC cell 9 and uses the same method as discussed with the apparatus shown in FIG. 3 for measuring the hemoglobin concentration.

In the preferred embodiment of the present invention, the bottom portion of WBC cell 9 and RBC cell 10 communicate with a closed waste liquid cell 14 through conduits 16a and 16b, respectively. Each of the conduits 16a and 16b are provided with an electromagnetic valves 15a and 15b, respectively, for controlling the communication of solution between WBC cell 9, RBC cell 10, and closed waste cell 14.

In the preferred embodiment, the Hgb measuring device 13 does not communicate directly with the waste cell 14. Instead, the Hgb measuring device 13 removes solution from WBC cell 9 through negative pressure supplied from constant volume syringe 19. Once the concentration of hemoglobin has been measured, a positive pressure is provided to Hgb measuring device 13 by constant volume syringe 19, and the measured solution is expelled back into WBC cell 9 for disposal.

Figure 3:
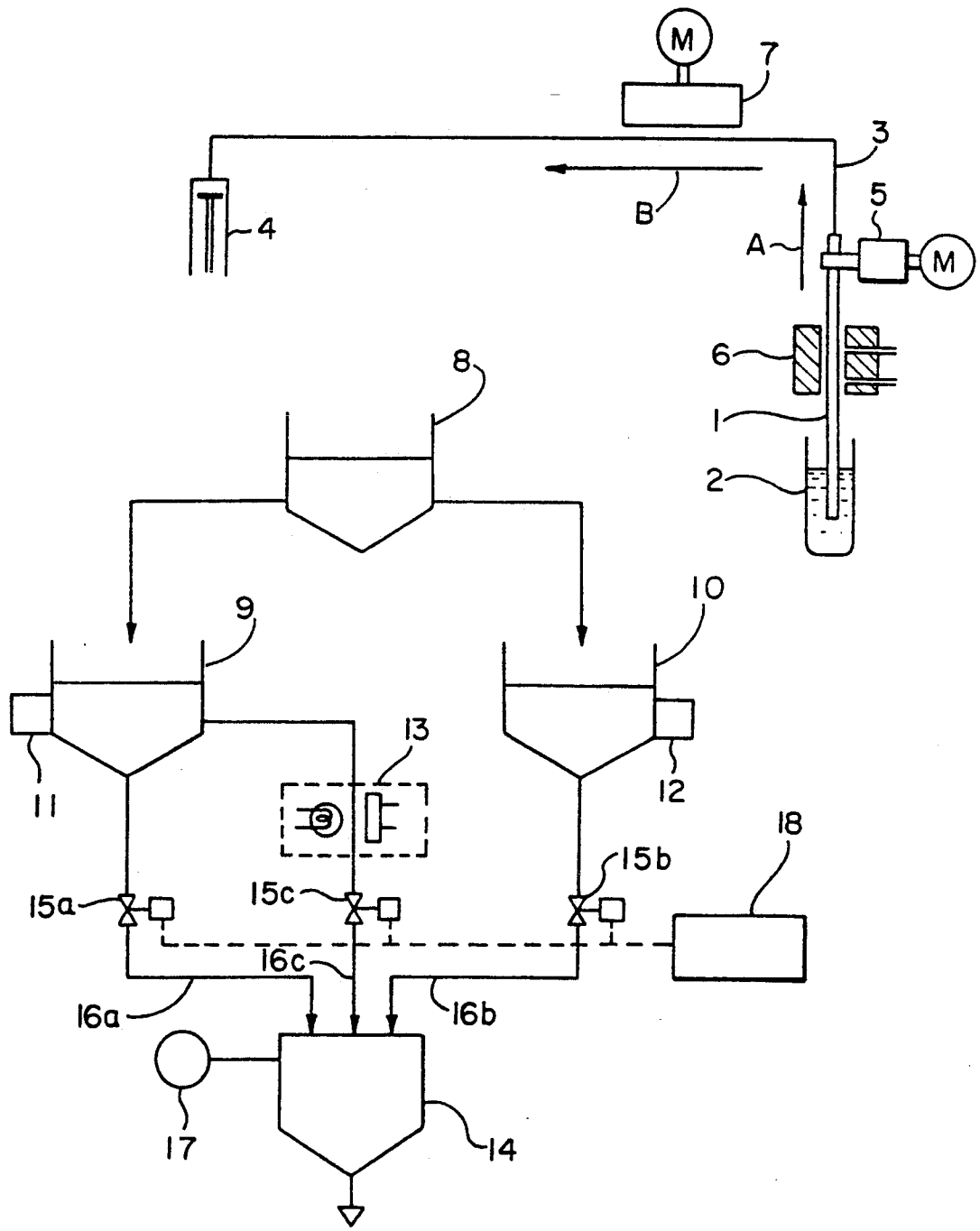
FIG. 3 is a block diagram showing a conventional apparatus for measuring and disposing of liquid blood.

In the preferred embodiment, liquid waste cell 14 is provided with a vacuum pump 17 to depressurize the liquid waste cell 14 and reduce the pressure in the same manner as discussed with the system shown in FIG. 3. However, in the preferred embodiment of the invention, liquid waste cell 14 is also provided with a pressure sensor 20, which detects the pressure within the waste cell 14.

In the preferred embodiment, a valve controlling circuit 21 controls the opening and closing of electromagnetic valves 15a and 15b. A reset signal a is provided to the valve controlling circuit 21 at the beginning of a waste solution collection cycle. When the reset signal a is applied, and the pressure level indicated by pressure sensor 20 rises to a preset level, the valve controlling circuit 21 closes valves 15a and 15b. The raised pressure level within liquid waste cell 14 corresponds to the point when waste cell 14 has accepted all of the solution from WBC cell 9 and RBC cell 10, emptying those treatment cells.

Also provided in the preferred embodiment is warning circuit 22. Warning circuit 22 keeps track of the lapse of time from the beginning of the solution collection cycle set by reset signal a and provides a warning signal when the pressure sensed by pressure sensor 20 does not rise to the preset level within a predetermined amount of time.

As shown in FIG. 2, valve controlling circuit 21 includes a comparator 23 and an RS flip-flop 24. The comparator 23 compares the pressure signal from pressure sensor 20, supplied as detected pressure voltage signal $V_0$, with a reference voltage $V_{ref}$. The reference voltage $V_{ref}$ is preset to be equivalent to a pressure level detected within the waste cell 14 corresponding to the point when WBC cell 9 and RBC cell 10 are emptied.

The output terminal of the comparator 23 is connected to the reset input terminal R of RS flip-flop 24. The set input terminal S of RS flip-flop 24 is connected to accept the solution collection cycle reset signal a. Thus, the RS flip-flop may be set by solution collection signal a, and then reset when the comparator determines that the pressure level within liquid waste cell 14 has risen above the predetermined value corresponding to voltage reference signal $V_{ref}$.

The Q output terminal of the RS flip-flop 24 is connected to electromagnetic valves 15 and 15b. When the Q output terminal is high, the electromagnetic valves 15a and 15b are opened. When the Q output terminal is set low in response to the comparator 23 resetting the flip-flop 24, the electromagnetic valves 15a and 15b will be closed.

The warning circuit 22 includes a clock generating circuit 26, a counter 27, an AND gate 28, and a buzzer 29. The counter 27 is connected to the clock generating circuit 26 so that the counter may count the clock pulses provided by the clock generating circuit 26.

The collection cycle reset signal a is also provided to the counter as a reset signal. Thus, at the beginning of the collection cycle, the counter 27 is reset to zero and begins to count up by counting the clock pulses provided by the clock generating circuit 26.

The output of the counter is provided to one of the inputs of AND gate 28, and the Q output from the RS flip-flop 24 is provided to the other input of AND gate 28. The buzzer 29 is driven by the output of AND gate 28. Thus, if the Q output is high and the counter 27 reaches the end of the count cycle, AND gate 28 will assert buzzer 29 and buzzer 29 will sound.

Prior to receiving the waste solution, the pressure within the waste cell 14 is reduced to an appointed level lower than ambient air pressure by vacuum pump 17. Once the pressure within the waste cell 14 has reached the predetermined low level, the collection cycle reset signal a is provided to valve controlling circuit 21. The Q output of RS flip-flop 24 is then sent to a high level, and the electromagnetic valves 15a and 15b are opened. As a result, the liquid waste solution which has already been treated and measured in WBC cell 9 and RBC cell 10 is sucked into the depressurized waste cell 14 through conduits 16a and 16b.

When the collection of waste solution is completed and the WBC cell 9 and RBC cell 10 become empty, the pressure within the liquid waste cell 14 suddenly begins to rise to a level of ambient air pressure. This sudden rise is detected by pressure sensor 20. Thus, an increased pressure detection signal $V_0$ is provided to comparator 23.

The increased pressure detection signal $V_0$ will exceed the reference voltage $V_{ref}$, and the output of comparator 23 will provide a high level signal to the reset terminal of RS flip-flop 24. As a result, the electromagnetic valves 15a and 15b will be closed. Thus, upon the completion of the collection of the treated solutions, the electromagnetic valve will close, closing communication to waste cell 14.

Additionally, the solution collection cycle reset signal a is also provided to counter 27 within warning circuit 22. As the collection cycle begins, the counter is reset to place a time limit upon the solution collection cycle. When the counter 27 counts a predetermined number of clock pulses from clock 26, the counter provides a high input to AND gate 28. If the solution collection cycle proceeds normally, and the waste liquid is collected in the waste cell 14, the Q output of flip-flop 24 will be set low prior to the counter 27 reaching the point where it inputs a high signal to AND gate 28. Thus, when the solution is smoothly collected within the liquid waste cell 14, AND gate 28 will never receive simultaneous high inputs, and the buzzer 29 will never sound.

However, if the conduits 16a and 16b become clogged during the waste solution collection cycle, the pressure within liquid waste cell 14 will never begin to rise at a sufficient speed to reset the flip-flop 24 before the counter 27 goes high. The Q output of the flip-flop will maintain a high input to AND gate 28 through the point in time when the counter 27 counts the elapsed time limit, and also provides a high input to AND gate 28. When this happens, the buzzer 28 will sound, indicating a failure in the solution collection cycle.

If it is determined that the quantity of solution within WBC cell 9 will be different from the quantity of solution within RBC cell 10, and one of the treatment cells will be emptied prior to the other, the coincidental timing of the opening and closing operation will be affected. The rapidity with which the waste vessel 14 raises pressure will no longer accurately reflect the waste collection cycle, and the valves will fail to operate within the cycle. In this instance, the opening and closing cycle of electromagnetic valves 15a and 15b, will be selectively switched so that the collection of solution from WBC cell 9 is separate from the collection of solution from RBC cell 10. In this manner, the valve controlling circuit 21 and warning circuit 22 are individually applied to the collection of solution in each of the treatment cells 9 and 10, respectively.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A system for removing blood samples from a measuring device comprising:
   a cell for receiving a blood sample to enable measuring procedures on the blood sample;
   a sealed waste receiving vessel connected to the cell;
   means for reducing the pressure within the sealed waste receiving vessel;

means for measuring the pressure within the receiving vessel and providing a pressure signal; and means for controlling the removal of the blood sample from the cells to the sealed waste receiving vessel in coordination with the pressure signal after the measuring procedures are completed.

2. A system for removing treated blood samples from a blood corpuscle concentration measuring device comprising:

a container for holding blood samples for measurement;

a closed vessel;

a pressurization means for controlling pressure within the closed vessel;

a pressure sensor for measuring pressure within the closed vessel and providing a signal;

a means for controlling fluid communication between the container and the closed vessel based upon the signal provided by the pressure sensor, the means for controlling including a valve controlling circuit for controlling an opening and closing operation of a valve disposed within a conduit, the conduit providing fluid communication between the container and the closed vessel, the valve controlling circuit indicating the beginning of a waste solution collection cycle and opening the valve; and a warning circuit for indicating a lapse of a predetermined time limit from the beginning of the waste solution collecting cycle.

3. The system of claim 2, wherein the container holds treated blood which has been measured to determine a concentration of blood corpuscles.

4. The system of claim 2, wherein the valves are electromagnetic valves.

5. The system of claim 2 wherein the warning circuit resets a beginning of the time limit in response to the valve controlling circuit indicating the beginning of a waste solution collection cycle.

6. An apparatus for measuring corpuscle concentration within blood samples, comprising:

a treating vessel for subjecting a sample to a measurement treatment;

a closed liquid waste vessel, the closed vessel receiving the treated sample through a conduit communicating with treating vessel;

a valve midway along the conduit, the valve opening and closing the conduit;

a pressure reducing means for reducing a pressure within the closed vessel to a first preset pressure level;

a pressure sensor for detecting the pressure within the vessel;

a valve controlling means for opening the valve to allow sample communication along the conduit and for closing the valve when the pressure sensor detects the pressure within the closed vessel has risen above a second preset level, the second preset level corresponding to an emptying of the treatment vessel; and an alarm providing an alarm signal when the pressure level does not rise to the second preset level within a predetermined time period from the opening of the valve.

* * * * *